United States Patent [19]

Wilczak

[11] Patent Number: 5,212,307

[45] Date of Patent: May 18, 1993

[54] LIGHT-SENSITIVE BIS-TRICHLOROMETHYL-S-TRIAZINES, AND PROCESS FOR THEIR PREPARATION

[75] Inventor: Wojciech A. Wilczak, Jersey City, N.J.

[73] Assignee: Hoechst Aktiengesellschaft, Frankfurt/Main, Fed. Rep. of Germany

[21] Appl. No.: 505,155

[22] Filed: Apr. 5, 1990

[30] Foreign Application Priority Data

Apr. 18, 1989 [DE] Fed. Rep. of Germany ....... 3912652

[51] Int. Cl.$^5$ ................. C07D 251/24; C07D 251/42
[52] U.S. Cl. .................... 544/194; 544/216; 544/1; 544/55; 544/96
[58] Field of Search ............. 544/194, 216, 1, 55, 544/96

[56] References Cited

U.S. PATENT DOCUMENTS

| | | | |
|---|---|---|---|
| 3,954,475 | 5/1976 | Bonham et al. | 96/67 |
| 3,987,037 | 10/1976 | Bonham et al. | 260/240 |
| 4,123,348 | 10/1978 | Wurfel | 208/10 |
| 4,189,323 | 2/1980 | Buhr | 430/281 |
| 4,619,998 | 10/1986 | Buhr | 544/193.1 |
| 4,696,888 | 9/1987 | Buhr | 430/270 |
| 4,837,128 | 6/1989 | Kawamma et al. | 430/281 |

FOREIGN PATENT DOCUMENTS

| | | |
|---|---|---|
| 0135348 | 3/1985 | European Pat. Off. . |
| 0135863 | 4/1985 | European Pat. Off. . |
| 3807381 | 9/1989 | Fed. Rep. of Germany . |
| 1584741 | 2/1981 | United Kingdom . |

OTHER PUBLICATIONS

Organic syntheses, coll. vol. III, 1955; 595–96 (1955).

*Primary Examiner*—John M. Ford
*Attorney, Agent, or Firm*—Foley & Lardner

[57] ABSTRACT

The invention describes light-sensitive bis-trichloromethyl-s-triazines of the general formula I

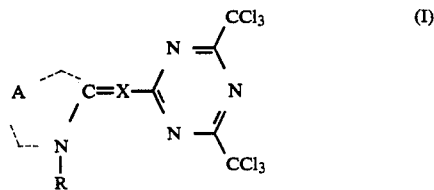

wherein A denotes the ring members required to complete a 5- or 6-membered heterocyclic ring which may be substituted or may carry a substituted or unsubstituted fused benzene ring, R denotes a substituted or unsubstituted alkyl group and X denotes CH or N.

The compounds are readily prepared in high yields. They are suitable for use as light-sensitive free-radical and acid donors in light-sensitive compositions.

21 Claims, No Drawings

LIGHT-SENSITIVE BIS-TRICHLOROMETHYL-S-TRIAZINES, AND PROCESS FOR THEIR PREPARATION

BACKGROUND OF THE INVENTION

The invention relates to 4,6-bis-trichloromethyl-s-triazines which are substituted in the 2-position and to a light-sensitive composition containing these compounds.

Compounds of the above-mentioned type are known for use as initiators for a number of photochemical reactions. They are employed, on the one hand, to utilize the free radicals formed under the action of actinic radiation for triggering polymerization reactions or color changes and, on the other hand, to initiate secondary reactions by means of the freed acid.

DE-C 22 43 621 (=U.S. Pat. No. 3,954,475) describes styryl-substituted trichloromethyl-s-triazines exhibiting a number of advantageous properties. However, it is a disadvantage of these compounds that their preparation is relatively complicated.

DE-C 27 18 259 (=U.S. Pat. No. 4,189,323) discloses 2-aryl-4,6-bis-trichloromethyl-s-triazines with polynuclear aryl groups, which have comparably good properties, in particular, a high sensitivity to light and which can be prepared by simpler methods. They are obtained by cotrimerization of trichloroacetonitrile with aromatically substituted acetonitriles, in a yield which is fairly high for this type of reaction. Certain amounts of by-products are, however, invariably formed, which must be separated from the desired compound.

Furthermore, DE-B 27 17 778 discloses light-sensitive compositions on a basis of unsaturated compounds or polymeric azides, which contain 2-heteroylcarbonyl-methylenebenzothiazoles or -benzoselenazoles as sensitizers.

DE-A 25 51 641 describes photopolymerizable compositions which contain photoinitiators comprising a combination of particular trihalomethyl-s-triazines with acylmethylene heterocycles, for example, benzoylmethylene benzothiazolines.

EP-A 135 348 and EP-A 135 863 disclose 1-alkyl-2-carbonylmethylene-benzothiazoles and similar heterocycles for use as photoinitiators, which carry a trichloromethylphenyl group on the carbonyl group.

DE-A 37 26 001 describes photopolymerizable compositions containing, as photoinitiators, bis-trihalomethyl-s-triazinylbenzenes which are further substituted by an amino group. The sensitivity of these compositions can be enhanced by adding sensitizers, such as Michler's ketone or benzoylene-ethylene-benzothiazoles.

EP-A 137 452 describes 2-(styrylphenyl)-4,6-bis-trichloromethyl-s-triazines as photoinitiators and photolytically activable acid donors.

German patent application P 38 07 381.1 of earlier date proposes similar compounds containing bis-trichloromethyl-s-triazine groups which form the external substituents on an aroylmethylene heterocycle.

Most of these compounds acting as photoinitiators are prepared by way of relatively complicated syntheses. Virtually all trichloromethyl-s-triazine derivatives which are customarily preferred due to their high activity are obtained by the above-mentioned method of cotrimerization of trichloroacetonitrile with other nitriles. It is, above all, the objective of the recent development of technology to provide well-known satisfactorily acting compounds or similar compounds by way of syntheses producing less by-products, the ecologically safe disposal of which gives rise to increasingly serious problems, as is known.

SUMMARY OF THE INVENTION

Accordingly, it is an object of the present invention to provide a light-sensitive substituted bis-trichloromethyl-s-triazine compound which has activity as a photoinitiator and acid donor comparable to known compounds of the same type, but which can be obtained in a simpler way and in higher yield.

Another object of the present invention is to provide a light-sensitive composition comprising the foregoing compound.

Still another object of the present invention is to provide a process for producing the novel compound.

In accomplishing the foregoing objectives, there has been provided, in accordance with one aspect of the present invention, a light-sensitive bis-trichloromethyl-s-triazine of the general formula I

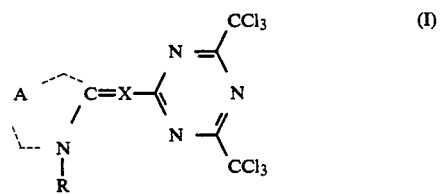

wherein
A denotes the ring members required to complete a 5- or 6-membered heterocyclic ring which may be substituted or may carry a substituted or unsubstituted fused benzene ring,
R denotes a substituted or unsubstituted alkyl group and
X denotes CH or N.

In accordance with another aspect of the present invention there is provided a light-sensitive composition comprising (a) a bis-trichloromethyl-s-triazine according to formula I above and (b) a compound which is capable of reacting with the photoreaction product of the triazine (a) to form a product whose light absorption or solubility in a developer is different from that of compound (b).

In accordance with still another aspect of the present invention, there is provided a process for the preparation of a compound according to formula I above, which comprises the step of reacting 2,4,6-tris-trichloromethyl-s-triazine with the salt of a quaternary N-heterocyclic base of the formula III or with a heterocyclic imine of the formula IV

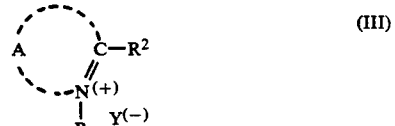

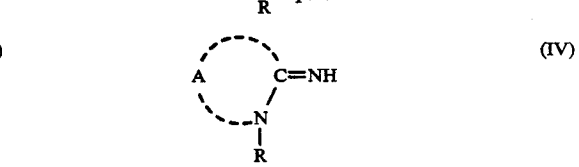

wherein
R is a methyl or amino group,
Y(−) is an anion and

A and R have the above-indicated significations.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modification.

DETAILED DESCRIPTION OF THE PREFERRED EMBODIMENTS

In the general formula I, A represents 3 or 4, preferably 3, ring members. Of the 5-membered heterocycles thus formed thiazoline or thiazolidine, respectively, is particularly preferred. The ring may be substituted, for example, by alkyl, aryl, alkoxy or aryloxy groups or by halogen atoms. It may preferably carry a fused benzene or naphthalene nucleus, in particular, a benzene nucleus which itself may carry substituents of the same type as those of the heterocyclic ring. Of the substituents mentioned, alkyl and alkoxy groups have generally 1 to 6 carbon atoms; their chains may be interrupted by ether oxygen atoms. The aromatic substituents have in general 6 to 10 carbon atoms. Further heteroatoms which, in addition to S, may be present in the 5- or 6-membered heterocycles are Se, O or N.

R is an unsubstituted or substituted alkyl group. Suitable substituents are, in particular, alkoxy, aryl or aryloxy groups or halogen atoms, alkoxy and aryl groups being preferred. Purely aliphatic substituents R normally may contain 1 to 6 carbon atoms, substituents R with aromatic fractions may have 7 to 10 carbon atoms. Examples of heterocyclic groups which are appropriately used for the present application are described in EP-A 135 863.

X is by preference a CH-group.

The starting material employed for the preparation of the compounds according to the present invention is tris-trichloromethyl-s-triazine. By trimerizing trichloroacetonitrile the compound is obtainable in known manner, in high, nearly quantitative yields [Bull. Chem. Soc. Jap. 42, 2924 (1969)]. It is reacted with a compound of one of the formulae III and IV to form a compound of the formula I, with elimination of HCl and, in the case of III, additionally HY. The reaction is advantageously run in a solvent and in the presence of a base. As anions Y of the quaternary base those of strong inorganic or organic acids, for example, of halohydric acids such as HCl, sulfuric acid or sulfonic acids, e.g. p-toluene sulfonic acid, are appropriately employed.

Suitable solvents comprise, for example, toluene, xylene, benzene, dimethyl formamide, diethyl ether, diisopropyl ether, methylene chloride, chloroform, pyridine, ethyl acetate, methanol, ethanol, tert. butanol and mixtures of substances of this kind.

Examples of suitable bases are tertiary amines such as triethylamine, dimethylbenzylamine, diethylbenzylamine, N-ethyldicyclohexylamine, N-ethylpiperidine, N-methylmorpholine, N-ethylpyrrolidone, 1,8-diazabicyclo[5.4.0]undec-7-ene, 1,4-diazabicyclo[2.2.2]octane or pyridine.

The reaction is preferably carried out at moderately elevated temperature, for example, in the range from about 20° to 60° C. As a rule, reaction is terminated after about 30 minutes. This reaction step also produces a very high yield which is, in most cases, nearly quantitative.

Suitable quaternary salts corresponding to formula III are described, for example, in J. Pharm. Soc. Jap. 1951, 71 and in Hamer, "Cyanine Dyes and Related Compounds", Interscience Publishers, 1964, pp. 116-147. Suitable heterocyclic imines corresponding to formula IV are described in Cressman, Org. Synth. Coll., Vol. III, page 595 (1955) and in U.S. Pat. No. 2,475,949.

Under the action of actinic radiation, in particular visible light and UV light, the compounds according to the invention form free radicals which are capable of initiating chemical reactions, in particular polymerizations initiated by free radicals. On irradiation, they also release hydrogen halide, by means of which acid-catalysed reactions, for example the cleavage of acetal bonds, or formation of salts, for example color changes of indicator dyes, can be set in motion.

The compounds according to the invention are suitable for use as photoinitiators for photopolymerizable layers which, as the essential constituents, contain monomers, binders and initiators.

Photopolymerizable monomers which can be used in this application are known and are described, for example, in U.S. Pat. No. 2,760,863 and 3,030,023.

The acrylates and methacrylates of polyhydric alcohols, such as diglycerol diacrylate and polyethylene glycol dimethacrylate, and acrylates and methacrylates of trimethylolethane, trimethylolpropane, pentaerythritol and of polyhydric alicyclic alcohols are preferred examples. Reaction products of the diisocyanates with partial esters of polyhydric alcohols are also used with advantage. Monomers of this type are described in DE-A 20 64 079, 23 61 041 and 28 22 190.

The amount of monomers in the layer is in general about 10 to 80% by weight, preferably 20 to 60% by weight.

A large number of soluble organic polymers can be employed as binders. Polyamides, polyvinyl esters, polyvinyl acetals, polyvinyl ethers, epoxide resins, polyacrylates, polymethacrylates, polyesters, alkyd resins, polyacrylamides, polyvinyl alcohol, polyethylene oxide, polydimethylacrylamide, polyvinylpyrrolidone, polyvinylmethylformamide, polyvinylmethylacetamide and copolymers of the monomers forming the homopolymers listed may be mentioned as examples.

Further binders are natural materials or processed natural materials, for example gelatine and cellulose ethers.

Advantageously, those binders are used which are water-insoluble but soluble or at least swellable in aqueous-alkaline solutions, since layers with such binders can be developed with the preferred aqueous-alkaline developers. Binders of this type can, for example, contain the following groups:

—COOH, —PO$_3$H$_2$, —SO$_3$H, —SO$_2$NH—, —SO$_2$N-HSO$_2$— and —SO$_2$—NH—CO—.

The following may be mentioned as examples of these: maleate resins, polymers of β-methacryloyloxyethyl N-(p-tolylsulfonyl)-carbamate and copolymers of these and similar monomers with other monomers as well as styrene/maleic anhydride copolymers. Alkyl methacrylate/methacrylic acid copolymers and copolymers of methacrylic acid, alkyl methacrylates and methyl methacrylate and/or styrene, acrylonitrile and others, as described in DE-A 20 64 080 and 23 63 806, are preferred.

The amount of binder is in general about 20 to 90% by weight, preferably 40 to 80% by weight, of the constituents of the layer.

Depending on the intended use and depending on the desired properties, the photopolymerizable compositions can contain various substances as additives. Examples are: inhibitors for preventing thermal polymerization of the monomers, hydrogen donors, substances which modify the spectral sensitivity of such layers, dyes, colored and colorless pigments, color precursors, indicators, plasticizers, and the like.

The light sensitivity of the photopolymerizable compositions of the present invention can be further increased by the addition of sensitizers. Suitable sensitizers are, for example, benzoin, benzoin derivatives, 9-fluorenone, 9-anthrone, 9,10-anthraquinone, xanthone and the substitution products thereof, thioxanthone, benzil, dibenzalacetone, p-dimethylamino-phenylstyrylketone, benzophenone, substituted benzophenones and, in particular, Michler's ketone. In addition, preference is given to sensitizers having the formula II

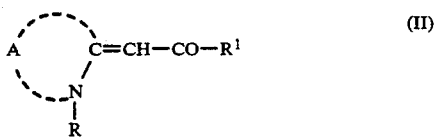

which are described, for example, in U.S. Pat. No. 3,870,524. In the formula, A and R have the significations indicated above, in connection with formula I. R' is an alkyl or aryl group. A preferred representative of this class of compounds is 2-benzoyl-methylene-3-methyl-naphtho[1,2-d]thiazoline.

Sensitization is particularly effective in compounds of the formula I, with $X=N$.

The photopolymerizable composition can be used for various applications, for example for the production of safety glass, of surface coatings which are cured by light or corpuscular radiation, for example electron beams, in the dental field and especially as a light-sensitive recording material in the reproduction field. The following may be mentioned as possible applications in this field: recording layers for the photomechanical production of printing forms for letterpress printing, planographic printing, gravure printing and screen printing, of relief copies, for example for the preparation of texts in Braille, of single copies, tanned images, pigment images and the like. Moreover, the compositions can be used for the photomechanical production of etch resists, for example for making name plates, printed circuits and for chemical milling.

The composition can be commercially used for the applications mentioned, in the form of a liquid solution or dispersion, for example as a photoresist solution, which is applied by the user himself to an individual support, for example for chemical milling and for the production of printed circuits, screen-printing stencils and the like. The composition can also be present as a solid light-sensitive layer on a suitable support in the form of a precoated, storable light-sensitive recording material, for example for the preparation of printing forms. It is also suitable for the preparation of dry resists.

In general, it is advantageous largely to protect the compositions from the influence of atmospheric oxygen during the photopolymerization. In the case of using the composition in the form of thin recording layers, it is advisable to apply a suitable covering film of low permeability for oxygen. This film can be self-supporting and can be peeled off before the recording layer is developed. For example, polyester films are suitable for this purpose. The covering film can also consist of a material which is soluble in the developer fluid or can at least be removed in the non-hardened areas during development. Examples of materials suitable for this purpose are polyvinyl alcohol, polyphosphates, sugars and the like.

Examples of suitable supports for the recording materials, produced with the composition according to the invention, are aluminum, steel, zinc, copper and plastics films, for example of polyethylene terephthalate or cellulose acetate, and screen-printing supports such as gauze polyamide 6.

The light-sensitive compounds are effective as photoinitiators even in concentrations of about 0.05% of total solids in the mass, and an increase to more than about 12% is in general inappropriate. Preferably, concentrations of 0.1 to 8% are used.

Moreover, the compounds according to the invention can also be used in those light-sensitive compositions in which a change in properties is initiated by acid catalysts formed during the photolysis of the initiator. For instance, the cationic polymerization of systems which contain vinyl ethers, N-vinyl compounds, such as N-vinylcarbazole, or special acid-sensitive lactones, may be mentioned here, and it is not excluded that free-radical processes also participate in some of these reactions. Further acid-hardenable compositions are aminoplasts, such as urea/formaldehyde resins, melamine/formaldehyde resins and other N-methylol compounds as well as phenol/formaldehyde resins. Even though the hardening of epoxy resins in general takes place by means of Lewis acids or acids, the anions of which are less nucleophilic than chloride and bromide, that is to say the anions of the hydrohalic acids which are formed during the photolysis of the novel compounds, layers which are composed of epoxy resins and novolaks are nevertheless readily hardened on exposure to light in the presence of the compounds according to the invention.

A further advantageous property of the novel compounds is their ability to cause color changes in colored systems during photolysis, namely to induce color formation from color precursors, for example leuco compounds, or to effect bathochromic color shifts and deepening in compositions which contain cyanine, merocyanine or styryl dye bases. Moreover, for example in the compositions described in DE-A 15 72 080, which contain a dye base, N-vinylcarbazole and a halogenohydrocarbon, the halogen compound tetrabromomethane can be replaced by a compound according to the invention in a quantity which is a fraction of the quantity of the former. Color changes are also desirable, for example in the production of printing forms, so that the result of copying can be assessed after exposure, even before development.

A particularly preferred field of application for the compounds according to the invention are compositions which, in addition to these compounds, contain a compound with at least one acid-cleavable —C—O—C grouping, as an essential component. The following may be mentioned in the first place as acid-cleavable compounds:

A) those having at least one orthocarboxylate and/or carboxamide acetal grouping, it also being possible for the compounds to have a polymeric character and for the said groupings to be present as linking elements in the main chain or as lateral substituents, and B) polymer compounds with recurring acetal and/or ketal groupings.

Type A acid-cleavable compounds, as components of radiation-sensitive compositions are described in detail in DE-A 26 10 842 or 29 28 636; compositions containing Type B compounds are the subject of DE-C 27 18 254.

As acid-cleavable compounds the specific aryl alkyl acetals and aminals of DE-C 23 06 248, which are likewise degraded by the photolysis products of the compounds according to the invention, may also be mentioned as examples.

Those compositions in which molecules are converted into smaller molecules directly or indirectly by the action of actinic radiation have in general an increased solubility, tackiness or volatility in the irradiated areas. These portions can be removed by suitable measures, for example they can be dissolved out with a developer fluid.

The novolak condensation resins, proven in many positive recording materials, have also proved to be particularly useful and advantageous as an additive when the compounds according to the invention are used in compositions with acid-cleavable compounds. They promote the strong differentiation between the exposed and unexposed layer portions on developing, in particular the relatively highly condensed resins with substituted phenols as the formaldehyde condensation partner. The nature and quantity of the novolak resins can vary depending on the intended purpose; quantities of novolak between about 30 and 90% by weight, particularly preferably 55-85% by weight, based on total solids are preferred.

In addition, a great number of other resins can also be included, preferably vinyl polymers, such as polyvinyl acetates, polyacrylates, polyvinyl ethers and polyvinylpyrrolidones, which in turn can have been modified by comonomers. The most advantageous proportion of these resins depends on the requirements in the particular application and the influence on the conditions of development and, in general, is not more than about 20% of the novolak. For special requirements, such as flexibility, adhesion and gloss etc., the light-sensitive composition can also contain small quantities of substances such as polyglycols, cellulose derivatives such as ethylcellulose, wetting agents, dyes and finely divided pigments as well as, when required, ultraviolet absorbers. Developing is preferably carried out with the aqueous-alkaline developers which are usual in industry and which can also contain small quantities of organic solvents, or with organic solvents.

The supports already listed in connection with the photopolymerizable compositions can also be used for positive-working recording materials and, in addition, the silicon and silicon dioxide surfaces conventionally used in microelectronics.

The quantity of the compounds according to the invention, used as photoinitiators, can vary between about 0.1 and 10%, preferably between about 0.2 to 5%, relative to total solids.

The light-sensitive compositions which contain one of the compounds according to the invention are preferably used in the production of printing forms, that is to say in particular offset printing forms, halftone gravure printing forms and screen-printing forms, in photoresist solutions and in so-called dry resists.

In the examples below, the invention is explained in further detail. First, compounds according to the invention, which were prepared and used in light-sensitive compositions, are compiled in a table. The method of preparation is illustrated in Preparation Examples 1 and 2, by means of Compounds 2 and 11. The examples which follow cover the application of some of the compounds in light sensitive compositions.

In the examples, quantities are given in parts by weight (pbw). Unless otherwise indicated, the percentages and quantities specified are to be understood as weight units.

TABLE

Compounds of the general formula I

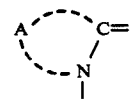

| | R | X |
|---|---|---|
| 1. thiazolidine | $C_2H_5$ | CH |
| 2. benzothiazoline | " | " |
| 3. naphtho[1,2-d]thiazoline | $CH_3$ | " |
| 4. benzothiazoline | " | " |
| 5. benzothiazoline | benzyl | " |
| 6. benzoselenazoline | $CH_3$ | " |
| 7. quinoline | $C_2H_5$ | " |
| 8. thiazolidine | benzyl | " |
| 9. benzothiazoline | methoxyethyl | " |
| 10. 6-methyl-benzoselenazoline | $CH_3$ | " |
| 11. benzothiazoline | $CH_3$ | N |

PREPARATION EXAMPLE 1

3-ethyl-2-(4,6-bis-trichloromethyl-s-triazin-2-yl-methylene)benzothiazoline (Compound 2)

Within a period of half an hour, 10 g (0.1 mol) of triethylamine was added dropwise to a suspension of 35 g (0.1 mol) of 3-ethyl-2-methyl-benzothiazolium-p-toluene-sulfonate and 43 g (0.1 mol) of tris-trichloromethyl-s-triazine in 300 ml of toluene. After completion of the addition the reaction mixture was stirred for half an hour, until the exothermic reaction ceased; the product which had precipitated was filtered off and dried. Compound 2 was obtained in nearly pure form in a quantity of 40 g. By evaporating the toluene in vacuo and treating the solid residue with ethanol, another 9 g of the product resulted. After recrystallization from 2-methoxy-ethanol 40 g (82%) of yellow needles of melting point 238° to 241° C. were obtained.

$\lambda_{max}$ (CHCl$_3$)=412 nm;

$^1$H NMR (CDCl$_3$): 1.47 (t, 3H); 4.25 (q, 2H); 6.21 (s, 1H); 7.16 (m, 4H) ppm Analysis (C$_{15}$H$_{10}$N$_4$SCl$_6$)

| | C | H | N | Cl |
|---|---|---|---|---|
| calc.: | 36.68 | 2.05 | 11.41 | 43.30 |
| found: | 36.4 | 1.9 | 11.3 | 43.1 |

PREPARATION EXAMPLE 2

3-methyl-2-(4,6-bis-trichloromethyl-s-triazin-2-yl-imino)benzothiazoline (Compound 11)

1.1 g (0.01 mol) of triethylamine was added dropwise to a solution of 4.3 g (0.01 mol) of tris-trichloromethyl-s-triazine and 1.7 g (0.01 mol) of 3-methyl-2-imino-benzothiazoline in 50 ml of toluene, at a temperature of about 50° C. The mixture was stirred for half an hour and the product which had precipitated was then filtered off and dried. 3 g of crude product was obtained and another 0.8 g was recovered from the mother lie. The crude yield of Compound 11 (3.8 g) was 79%. After recrystallization from ethanol, cream-colored crystals of melting point 251° to 253° C. were obtained.

$\lambda_{max}$ (CHCl$_3$)=352 nm $^1$H NMR (CDCl$_3$):4.07 (s, 3H); 7.47 (m, 4H)

Analysis (C$_{13}$H$_7$N$_5$SCl$_6$):

|  | C | H | N | Cl |
|---|---|---|---|---|
| calc.: | 32.66 | 1.48 | 14.65 | 44.5 |
| found: | 32.5 | 1.3 | 14.5 | 44.4 |

Application Example 1

A solution comprising 1.40 pbw of the polyacetal obtained from 2-ethyl-butyraldehyde and triethylene glycol, 4.70 pbw of a cresol-formaldehyde novolak, melting range from 105 to 120° C., 0.23 pbw of Compound 5 and 0.02 pbw of crystal violet base in 45 pbw of propylene glycol monomethyl ether, 28 pbw of tetrahydrofuran and 20 pbw of dimethyl formamide was applied by spin-coating to a plate of electrolytically grained and anodically oxidized aluminum. After drying, the light-sensitive layer had a weight of 2.0 g/m$^2$. Using a 5000 W metal halide lamp the plate was contact-exposed for 30 seconds under a transparency which contained a step wedge with density increments of 0.15. After a waiting time of 10 minutes, the plate was developed for 1 minute using the following solution:

5.5 g of sodium metasilicate·9 H$_2$O.

3.4 g of trisodium phosphate·12 H$_2$O, 0.4 g of sodium dihydrogen phosphate (anhydrous) and 90.7 g of water.

A positive image was obtained, which had been fully developed up to step 4.

APPLICATION EXAMPLE 2

A solution comprising 4.30 pbw of a phenol-formaldehyde novolak, 10.60 pbw of N-vinylcarbazole, 0.24 pbw of 2-(p-dimethylamino-styryl)benzothiazole and 0.25 pbw of Compound 2 in 84.60 pbw of butanone was applied by spin-coating to an electrolytically grained and anodically oxidized aluminum plate and dried. The dry layer weight was 1.5 g/m$^2$. The plate was exposed as in Application Example 1 and, in the process, the color of the exposed areas changed from yellow to orangered.

The non-exposed layer areas were washed out by treating the plate with the developer specified in Application Example 1.

APPLICATION EXAMPLE 3

A solution comprising 1.60 pbw of the esterification product obtained from
  1 mol of 2,3,4-trihydroxybenzophenone and
  3 mols of 1,2-naphthoquinone-2-diazide-5-sulfonyl chloride, 6.60 pbw of the novolak used in Application Example 1, 0.22 pbw of Compound 1 and 0.075 pbw of crystal violet in 50.00 pbw of propylene glycol monomethyl ether and 50.00 pbw of dimethyl formamide was applied by spin-coating to an electrolytically grained and anodically oxidized aluminum plate and dried. The layer weight was 2.3 g/m$^2$. The plate was exposed for 60 seconds under a step wedge, using the light source specified in Application Example 1. The image obtained exhibited a readily visible contrast. The plate was then treated for 60 seconds with the following developer:

8.5 g of Na$_2$SiO$_3$·9 H$_2$O, 0.8 g of NaOH, 1.5 g of Na$_2$B$_4$O$_7$·10 H$_2$O and 9.2 g of water.

A positive image of the original was obtained, in which step 5 was clear.

APPLICATION EXAMPLE 4

The procedure of Application Example 3 was followed, but instead of Compound 1 one of Compounds 5 and 11 was used. In both cases, the images obtained showed a good exposure contrast and had 5 clear steps. Similar results were obtained when one of Compounds 8, 9 and 10 was employed.

APPLICATION EXAMPLE 5

The procedure of Application Example 2 was followed, but instead of the 2-(p-dimethylaminostyryl)benzothiazole the same quantity of Sudan Yellow was used. After imagewise exposure, the exposed areas showed a red coloration. Similar results were obtained by substituting Compounds 6, 7, 3 or 4 for Compound 2.

APPLICATION EXAMPLE 6

A solution comprising 7.1 pbw of pentaerythritol triacrylate, 6.0 pbw of a methyl methacrylate/methacrylic acid copolymer (acid number 115), 0.15 pbw of Compound 1 and 0.3 pbw of an azo dye, obtained by coupling of 2,4-dinitro-6-chlorobenzene-diazonium salt with 2-methoxy-5-acetylamino-N-hydroxyethyl-N-cyanoethyl-aniline in 65 pbw of 2-methoxyethanol and 23 pbw of butyl acetate was applied by spin-coating to an electrolytically grained and anodically oxidized aluminum plate and dried. The layer weight was 1.5 g/m$^2$. The light-sensitive layer was coated with a thin layer of polyvinyl alcohol.

The plate was exposed as described in Application Example 3 and developed for 45 seconds in a 1.5% strength aqueous sodium metasilicate solution. Four fully crosslinked wedge steps were obtained.

APPLICATION EXAMPLE 7

A solution comprising 32.5 pbw of a 30.4% strength solution in butanone, of a terpolymer prepared from styrene, n-hexylmethacrylate and methacrylic acid (10:60:30) and having an acid number of 190, 10.0 pbw of the diurethane obtained from 1 mol of 2,2,4-trimethyl-hexamethylene-diisocyanate and 2 mols of hydroxyethyl methacrylate, 0.025 pbw of crystal violet base, 0.4 pbw of Compound 11 and 0.4 pbw of 2-benzoylmethylene-3-methyl-naphtho[1,2-d]-thiazoline in 70 pbw of dimethyl formamide and 70 pbw of 2-methoxy ethanol was applied by spin-coating to a plate of electrolytically grained and anodically oxidized aluminum and dried. The layer weight was 1.6 g/m$^2$. The light-sensitive layer was then coated with a thin layer of polyvinyl alcohol. The plate was exposed for 2 seconds under a step wedge, using the light source specified in Application Example 1. It was then heated for 1 minute at 100° C. and manually developed within 45 seconds using the following solution:

12 g of sodium metasilicate·9 H$_2$O, 2.13 g of strontium chloride, 1.2 g of a non-ionogenic wetting agent (coconut oil alcohol-polyoxyethylene ether having about 8 oxyethylene groups) and 0.12 g of an anti-foam agent on a basis of silicone in 4000 g of water.

After development 10 fully crosslinked wedge steps were obtained.

What is claimed is:

1. A light-sensitive bis-trichloromethyl-s-triazine having the formula I

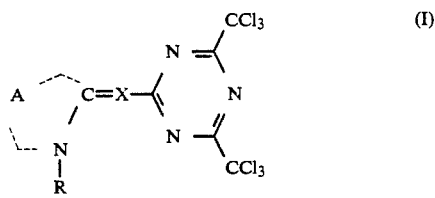

wherein

A are the ring members required to complete a 5- or 6-membered heterocyclic ring, wherein said ring members may be unsubstituted or substituted with an alkyl or alkoxy group containing 1 to 6 carbon atoms, an aryl or aryloxy group containing 6 to 10 carbon atoms or a halogen atom, wherein said heterocyclic ring may be fused to a benzene or naphthalene ring, and wherein said fused benzene or naphthalene ring may be unsubstituted or substituted with an alkyl or alkoxy group containing 1 to 6 carbon atoms, an aryl or aryloxy group containing 6 to 10 carbon atoms or a halogen atom is an alkyl group unsubstituted or substituted with an alkoxy group having 1 to 6 carbon atoms, an aryl or aryloxy group having 7 to 10 carbon atoms or halogen, and X is CH or N.

2. A bis-trichloromethyl-s-triazine as claimed in claim 1, wherein A represents 3 ring members.

3. A light-sensitive bis-trichloromethyl-s-triazine having the formula I

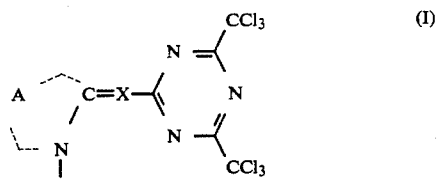

wherein

A are the ring members required to complete a 5- or 6-membered heterocyclic ring, wherein said ring members may be unsubstituted or substituted with an alkyl or alkoxy group containing 1 to 6 carbon atoms, an aryl or aryloxy group containing 6 to 10 carbon atoms or a halogen atom wherein said heterocyclic ring may be fused to a benzene or naphthalene ring, and wherein said fused benzene or naphthalene ring may be unsubstituted or substituted with an alkyl or alkoxy group containing 1 to 6 carbon atoms, an aryl or aryloxy group containing 6 to 10 carbon atoms or a halogen atom, with the proviso that A contains at least one heteroatom selected from the group consisting of S, Se, O, and N, wherein the additional heteroatom is in a 1,3 relationship to the N that is already present in the ring, R is an alkyl group unsubstituted or substituted with an alkoxy group having 1 to 6 carbon atoms, an aryl or aryloxy group having 7 to 10 carbon atoms, or halogen, and X is CH or N.

4. A bis-trichloromethyl-s-triazine as claimed in claim 3, wherein said heterocyclic ring is selected from the group consisting of thiazoline and thiazolidine.

5. A bis-trichloromethyl-s-triazine as claimed in claim 4, wherein said heterocyclic ring is a thiazoline ring.

6. A bis-trichloromethyl-s-triazine as claimed in claim 1, wherein said heterocyclic ring is substituted with an alkyl or alkoxy group containing 1 to 6 carbon atoms, an aryl or aryloxy group containing 6 to 10 carbon atoms, or a halogen atom.

7. A bis-trichloromethyl-s-triazine as claimed in claim 1, wherein said heterocyclic ring is fused to a benzene or naphthalene nucleus.

8. A bis-trichloromethyl-s-triazine as claimed in claim 7, wherein said heterocyclic ring is fused to a benzene ring which is substituted with at least one substituent R.

9. A bis-trichloromethyl-s-triazine as claimed in claim 7, wherein at least one of said heterocyclic ring, said benzene nucleus, and said naphthalene nucleus is substituted with an alkyl or alkoxy group containing 1 to 6 carbon atoms, an aryl or aryloxy group containing 6 to 10 carbon atoms, or a halogen atom.

10. A bis-trichloromethyl-s-triazine as claimed in claim 1, wherein said heterocyclic ring is unsubstituted.

11. A bis-trichloromethyl-s-triazine as claimed in claim 1, wherein R is unsubstituted.

12. A bis-trichloromethyl-s-triazine as claimed in claim 1, wherein R is substituted with an alkoxy group having 1 to 6 carbon atoms, an aryl or aryloxy group having 7 to 10 carbon atoms, or a halogen.

13. A bis-trichloromethyl-s-triazine as claimed in claim 1, wherein X is said CH group.

14. A process for producing a compound having the formula I as claimed in claim 1, comprising the step of reacting 2,4,6-tris-trichloromethyl-s-triazine with a salt of a quaternary N-heterocyclic base of the formula III or with a heterocyclic imine of the formula IV

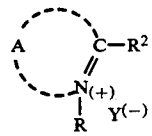         (III)

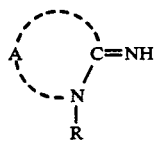         (IV)

in which
R$^2$ is a methyl or amino group,
Y$^{(-)}$ is an anion, and
A and R are as defined in claim 1.

15. A process as claimed in claim 14, wherein said reaction is carried out in the presence of a base.

16. A process as claimed in claim 15, wherein said base employed is a tertiary amine.

17. A process as claimed in claim 14, wherein said reaction is carried out in a solvent.

18. A process as claimed in claim 14, wherein said reaction is carried out at an elevated temperature.

19. A process as claimed in claim 14, wherein compound (III) is used.

20. A process as claimed in claim 14, wherein compound (IV) is used.

21. A process as claimed in claim 18, wherein said temperature is between about 20° to 60° C.

* * * * *

UNITED STATES PATENT AND TRADEMARK OFFICE
CERTIFICATE OF CORRECTION

PATENT NO. : 5,212,307
DATED     : May 18, 1993
INVENTOR(S) : Wojciech A. WILCZAK It is certified that error appears in the above-indentified patent and that said Letters Patent is hereby corrected as shown below:

Claim 1, column 11, line 61, "atom" should read "atom," and
Claim 1, column 11, line 62, "is an" should read --R is an--.

Signed and Sealed this

Seventeenth Day of May, 1994

Attest:

BRUCE LEHMAN

*Attesting Officer*  *Commissioner of Patents and Trademarks*